(12) United States Patent
Stanier

(10) Patent No.: US 9,968,802 B2
(45) Date of Patent: May 15, 2018

(54) SILICAS

(75) Inventor: Peter William Stanier, Cheshire (GB)

(73) Assignee: PQ Silicas UK Limited, Warrington Cheshire (GB)

( * ) Notice: Subject to any disclaimer, the term of this patent is extended or adjusted under 35 U.S.C. 154(b) by 0 days. days.

(21) Appl. No.: 12/158,234

(22) PCT Filed: Dec. 12, 2006

(86) PCT No.: PCT/GB2006/004649
§ 371 (c)(1),
(2), (4) Date: Sep. 12, 2008

(87) PCT Pub. No.: WO2007/068916
PCT Pub. Date: Jun. 21, 2007

(65) Prior Publication Data
US 2009/0010973 A1  Jan. 8, 2009

(30) Foreign Application Priority Data
Dec. 14, 2005  (GB) .................................. 0525369.5

(51) Int. Cl.
*A61Q 11/00* (2006.01)
*A61K 8/25* (2006.01)
*C01B 33/193* (2006.01)

(52) U.S. Cl.
CPC ................ *A61Q 11/00* (2013.01); *A61K 8/25* (2013.01); *C01B 33/193* (2013.01); *A61K 2800/412* (2013.01); *Y10T 428/2982* (2015.01)

(58) Field of Classification Search
CPC ...... A61K 8/25; A61K 2800/412; A61K 9/14; A61Q 11/00; Y19T 428/2982; B02C 19/09; B02C 23/08
USPC ............... 423/335, 336, 337, 338, 339, 340; 424/49, 724; 106/287.34; 524/493; 428/404
See application file for complete search history.

(56) References Cited

U.S. PATENT DOCUMENTS

| | | | |
|---|---|---|---|
| 4,303,641 A | 12/1981 | DeWolf, II et al. | |
| 4,612,189 A | 9/1986 | Oyobe et al. | |
| 5,098,695 A | 3/1992 | Newton et al. | |
| 5,447,704 A | 9/1995 | Aldcroft et al. | |
| 5,589,160 A | 12/1996 | Rice | |
| 5,603,920 A | 2/1997 | Rice | |
| 5,658,553 A | 8/1997 | Rice | |
| 5,939,051 A | 8/1999 | Santalucia et al. | |
| 5,964,937 A | 10/1999 | Stanier | |
| 6,399,111 B1 * | 6/2002 | Stanier ........................ | 424/724 |
| 6,419,174 B1 | 7/2002 | McGill et al. | |
| 6,585,960 B2 * | 7/2003 | Thomas et al. ................ | 424/49 |
| 7,166,272 B2 | 1/2007 | Fujisawa | |
| 7,662,363 B2 | 2/2010 | Stanier et al. | |
| 2003/0131536 A1 * | 7/2003 | Kostinko et al. ............... | 51/308 |
| 2006/0008422 A1 * | 1/2006 | Araya ....................... | A61K 8/25 424/49 |
| 2006/0027142 A1 * | 2/2006 | Huang ......................... | 106/437 |
| 2006/0140877 A1 | 6/2006 | McGill et al. | |

FOREIGN PATENT DOCUMENTS

| | | |
|---|---|---|
| EP | 0 236 070 A2 | 9/1987 |
| EP | 0236070 A2 | 9/1987 |
| EP | 0308165 A2 | 3/1989 |
| EP | 0535943 A1 | 4/1993 |
| EP | 1 410 789 A1 | 4/2004 |
| EP | 1410789 | 4/2004 |
| EP | 1410789 A1 * | 4/2004 |
| GB | 1186706 | 4/1970 |
| GB | 1264292 | 2/1972 |
| JP | 56-034617 | 4/1981 |
| JP | 06-183721 | 7/1994 |
| JP | 2002275389 | 9/2002 |
| JP | 2005-512936 A1 | 12/2005 |
| RU | 2171781 C2 | 2/2000 |
| RU | 2155579 | 9/2000 |
| RU | 2295948 | 3/2007 |
| WO | 92/02454 A1 | 2/1992 |
| WO | 94/10087 A1 | 5/1994 |
| WO | 96/34592 A1 | 11/1996 |
| WO | 96/34594 | 11/1996 |
| WO | 99/51196 A1 | 10/1999 |
| WO | 03/042293 A1 | 5/2003 |
| WO | 2005/065634 A1 | 7/2005 |
| WO | 2005/067876 A1 | 7/2005 |
| WO | 2006/071528 A1 | 7/2006 |

OTHER PUBLICATIONS

PCT/GB2002/005425. Jul. 2002, Stainer, Peter, English translation provided.*
Office Action issued for JP 2008-545084 (translation) dated Jul. 17, 2012.
Office Action dated Jul. 14, 2010 by the Chinese Patent Office for Chinese Pat. App. No. 2006800469111 (English Translation).
Decision on Grant Patent for Invention (Translation) for RU Patent App. No. 2008128435/15(035016).
Office Action issued for EP 06 020 508.3-1218 dated Feb. 4, 2010.

* cited by examiner

*Primary Examiner* — Melvin C. Mayes
*Assistant Examiner* — Smita S Patel
(74) *Attorney, Agent, or Firm* — Buchanan Ingersoll & Rooney PC

(57) ABSTRACT

An amorphous precipitated silica with controlled abrasivity and effective cleaning properties for use in an oral composition produced through comminution and classification of the silica to form particles with an oil absorption value of 150 cm$^3$/100 g or less, a weight median particle diameter dso of less than 3 μm and a dgo value, wherein 90% by weight of the particles have a diameter less than the dgo value, of 6 μm or less.

20 Claims, No Drawings

SILICAS

This invention relates to precipitated amorphous silica particles of use, for example, as abrasive agents in oral compositions. The invention also relates to processes for preparing the abrasives and to oral compositions, such as toothpastes, which clean teeth without excessive abrasion of dentine or enamel.

Oral compositions, such as toothpastes, are well characterised in the literature and many compositions are disclosed in patent specifications and other literature. They are used to aid in the removal of food particles, staining and bacterial films from the surfaces of teeth. Abrasives are formulated into toothpastes as the main cleaning agent. Commonly used abrasives are aluminas, calcium carbonates and calcium phosphates. More recently synthetic silicas have been adopted because of their efficient cleaning, compatibility with other ingredients and other physical properties such as refractive index.

In order to achieve cleaning, it has been generally accepted that the abrasive must provide a certain degree of abrasiveness of the tooth surface. This abrasiveness must be kept at a sufficiently low level that the surfaces of teeth, particularly dentine, are not permanently damaged by daily brushing regimes. The rate of enamel removal should not exceed the rate of natural replenishment through remineralisation.

A general problem with abrasive cleaning systems, and toothpaste abrasives in particular, is the proportionate relationship between cleaning and abrasion: it is accepted that any change in the nature or amount of abrasive in a composition that leads to improved cleaning will generally also lead to higher abrasion of the surface to be cleaned. This is particularly undesirable when that surface is the surface of a tooth. By corollary, it is also generally accepted that any reduction in abrasion from a cleaning composition will cause a fall in cleaning performance. So, in Morton Pader's textbook "Oral Hygiene Products and Practice" (Cosmetic Science and Technology Series vol. 6, 1987, pages 248-249) it is stated that as dentifrice abrasiveness increased, less stained pellicle formed on clean teeth and more stained pellicle was removed from pre-stained teeth. This correlation between the values of cleaning power and abrasivity (expressed as RDA value—Radioactive Dentine Abrasion test value) for abrasive systems was used as the basis of accepting RDA as the monitor of the cleaning power of an oral composition.

Synthetically produced amorphous silicas are often the favoured abrasive component in oral compositions and can be readily tailored during the production process to possess predetermined abrasive and other physical characteristics appropriate for use in oral compositions. Precipitated silicas are particularly useful as abrasive components.

It would be highly desirable to provide suitable abrasives, which break the correlation between cleaning and abrasion, particularly for use in oral compositions for cleaning teeth, where abrasion and erosion of the gum tissue or tooth surface can lead to problems such as excessive sensitivity to heat or cold or cavities. It would also be highly desirable to reduce the abrasivity of existing silicas, without the need for modification of the chemical processing leading to precipitation of the silica, and without loss in cleaning power in dentifrices from the silica.

WO 2005/067876 A1 and WO 2005/065634 disclose a precipitated silica for use as a cleaning booster with a medium to high RDA, typically from 100 to 220, and an oil absorption of from 50 to 130 $cm^3/100$ g. The silica has a preferred weight mean particle size of at least 2 μm, more usually at least 3 μm as measured by Malvern Mastersizer™. The desired particle size of the silica is obtained by subjecting the silica to a micronising comminution step. There is no mention in these documents of tailoring the particle size distribution of the silica, by limiting the volume of particles above certain particle diameters, in order to obtain good cleaning at low abrasion from an oral composition.

A first aspect of the invention provides amorphous precipitated silica particles with an oil absorption value of 150 $cm^3/100$ g or less, a weight median particle diameter $d_{50}$ of less than 3 μm and a $d_{90}$ value, wherein 90% by weight of the particles have a diameter less than the $d_{90}$ value, of 6 μm or less.

Preferably the amorphous precipitated silica particles are of medium structure, low structure or very low structure. The most preferred silicas of the invention for cleaning have a very low structure. The structure of precipitated silicas is related to the packing of the aggregated particles and can be measured using a variety of techniques, including oil absorption and mercury intrusion porosimetry. This is discussed in "Cosmetic properties and structure of fine-particle synthetic precipitated silicas" by S. K. Wason; J. Soc. Cosmet. Chem, 29, 497-521 (August 1978).

The silica particles of the invention provide a novel range of properties, combining controlled low abrasivity coupled with excellent cleaning performance, particularly in an oral composition such as a toothpaste.

Precipitated silica abrasives and methods for their preparation are known in the art. Alkaline metal silicate solution is mixed with acid, optionally in the presence of an electrolyte, stirring and filtering out the precipitated silica. The resulting precipitate filter cake is than washed, dried and comminuted to the desired size. Precipitated silicas are prepared, for example, in accordance with general methods in U.S. Pat. No. 5,447,704 issued $5^{th}$ September 1995 to Aldcroft et al and European Patent EP 0 308 165 A1 Aldcroft et al, published 22 Mar. 1989 the processes of which are herein incorporated by reference.

U.S. Pat. No. 5,447,704 discloses a method of preparing an amorphous precipitated silica, suitable for use as a toothpaste abrasive, and having:
i) a surface area in the range from about 10 to about 450 $m^2/g$,
ii) a weight mean particle size in the range from about 3 to about 20 microns,
iii) a perspex abrasion value in the range from about 23 to about 35, and optionally,
iv) an oil absorption in the range from about 60 to about 110 $cm^3/100$ g which is produced by the reaction of sodium silicate, having a silica:$Na_2O$ ratio in the range from 1.8:1 to 3.5:1, with mineral acid, with the concentration and volume of the reactants controlled to give a reaction in the pH range from about 10 to about 10.5, in the presence of a water soluble electrolyte comprising a cation selected from the group comprising aluminium, magnesium, calcium, sodium and potassium with an associated anion selected from the group comprising bromide, carbonate, chloride, nitrate, acetate and sulphate wherein the electrolyte:silica weight ratio is from about 0.1:1 to about 2:1, the precipitation reaction being performed in the temperature range of about 95° C. to about 100° C.

Optionally the reaction medium is subjected to a hydrothermal ageing step during the final acid addition step to provide materials with lower surface areas.

EP 0 308 165 includes a method of preparing amorphous silicas, especially precipitated silicas, suitable for use as a toothpaste abrasive, and having i) a BET surface area in the range from about 420 to about 550 m$^2$/g,
ii) a weight mean particle size in the range from about 5 to about 20 microns,
iii) a perspex abrasion value in the range from about 15 to about 28,
iv) a mean pore diameter in the range from about 3.0 to about 8.0 nm,
v) a transmission of at least about 70% in the refractive index range of 1.444 to 1.460, which is produced by the reaction of sodium silicate, having a silica:Na$_2$O ratio in the range from 3.2:1 to 3.4:1, with mineral acid, with the concentration and volume of the reactants controlled to give a reaction in the pH range from about 10 to about 10.5, in the presence of a water soluble electrolyte comprising a cation selected from sodium and potassium with an associated anion selected from chloride and sulphate wherein the electrolyte:silica weight ratio is from about 0.4:1 to about 1.2:1, the precipitation reaction being performed in the temperature range of about 45° C. to about 55° C., the pH of the reaction medium then being made acidic by addition of a mineral acid, separating and washing the resultant silica product. Optionally the reaction medium is subjected to a hydrothermal ageing step during the final acid addition step to provide materials with lower surface areas.

Conventionally a mechanical mill, such as a hammer mill, is used in order to comminute the precipitated silica after washing and drying. This form of milling generally yields weight median particle diameters of the order of 20 to 7 μm. In order to achieve the smaller particle sizes required for the precipitated silicas of the invention, a considerably more energy intensive comminution process is needed. A suitable process for obtaining precipitated amorphous silica particles of the invention is micronisation using a jet or pancake microniser, or fluidised bed micronisation, including opposed jet micronisers. Optionally, the material may be subjected to classification, screening or sieving at any stage of the process in order to optimize the process and to remove excess large particles such that the preferred particle size distributions of the silica particles of the invention may be obtained.

The preferred process for micronisation of the silica particles in order to obtain the required weight median particle diameter is carried out using a fluid energy mill or microniser with integral air classifier. The fluid energy is normally air, but can also be superheated steam, especially if a higher energy input is required.

The weight median particle diameter of the silica particles is determined by laser diffraction using a Malvern Mastersizer model S, with a 300 RF lens (measurement range 0.05-3480 μm), Malvern Mastersizer software v 2.18 and a DIF 2012 dispersion unit. This instrument, made by Malvern Instruments, Malvern, Worcestershire, utilises Mie theory to calculate the particle size distribution. Mie theory predicts how light is scattered by spherical particles and takes into account the refractive index of the particles. The real value used for silica refractive index is 1.4564 and 0.1 for the imaginary refractive index of the particle (the absorption of light), with water dispersant at 1.33 refractive index.

Before measurement, the sample is dispersed ultrasonically in water for 2.5 minutes on a 50% power setting to form an aqueous suspension. The pump speed i.e. the speed at which the dispersed sample is passed through the instrument, is set at 50% (1250+/−20 r.p.m.) The stirrer speed i.e. the speed at which the silica particles are stirred within the disperser unit, is set at 50% (530+/−5 r.p.m.). Low power 2-5 mW He/Ne laser light (wavelength 632.6 nm) is passed through a flow cell containing the particles dispersed in de-ionised water. The scattered light intensity is measured as a function of angle and this data is used to calculate an apparent particle size distribution. The volume and hence weight median particle diameter ($d_{50}$) or 50 percentile, and the volume and hence weight percentage of material below any specified size (such as $d_{90}$ and $d_{99}$) are easily obtained from the data generated by the instrument, assuming constant density for the particles. Throughout the description, weight based particle size measures are used, assuming constant density, but alternatively, these can be expressed as volume-based particle size measures, without any density assumptions.

Suitably, the particles of the invention have a weight median particle diameter $d_{50}$ of less than 3 μm, preferably less than 2.8 μm, more preferably less than 2.5 μm. The median particle diameter is the diameter such that there are equal weights of particles less than the median diameter and greater than the median diameter (as determined by light scattering measurement as detailed herein).

For the amorphous precipitated silica particles of the invention, there are relatively few silica particles of large particle size present, as these can lead to increased scratching, abrasion and poor mouth feel when the abrasive is used in an oral composition such as a toothpaste. Hence the $d_{90}$ value for the silica particles (the $d_{90}$ value is the diameter where 90% by weight of particles have a diameter less than the $d_{90}$ diameter value) is 6 μm or less, even more preferably 5 μm or less, even more preferably 4.5 μm or less. It is also preferred if the $d_{99}$ value for the silica particles (the $d_{99}$ value is the diameter where 99% by weight of particles have a diameter less than the $d_{99}$ diameter value) is 12 μm or less, more preferably 10 μm or less, even more preferably 9 μm or less, most preferably 7 μm or less.

Suitably, the $d_{50}$ value of the amorphous precipitated silica particles of the invention is 0.5 μm or more, preferably 1 μm or more. Suitably, the $d_{90}$ value of the amorphous precipitated silica particles of the invention is 2 μm or more. Suitably, the $d_{99}$ value of the amorphous precipitated silica particles of the invention is 3 μm or more. Lower values can lead to loss in cleaning power.

The amorphous precipitated silica particles of the invention are preferably in a relatively dry state to ensure a free flowing powder with no microbial and preservation issues. Suitably, the physical moisture content of the particles of the invention is 25% by weight or less, preferable 15% by weight or less, more preferably 5% by weight or less. Suitably, the material is dried prior to comminution Physical moisture content is determined by the loss in weight of the silica particles when dried to constant weight in an electric oven at 105° C.

Suitable precipitated silica particles of the invention will have a Perspex Abrasion Value less than 20, preferably less than 16, more preferably less than 15, even more preferably less than 10.

The Perspex® Abrasion Value test (PAV) is used to measure the abrasiveness of an abrasive particle for use in a toothpaste. This test is based upon a toothbrush head brushing a Perspex® plate in contact with a suspension of the silica in a sorbitol/glycerol mixture. Perspex® has a similar hardness to dentine, so an abrasive system which produces scratches on Perspex® is likely to have a similar effect on dentine. The slurry composition is as follows:

Silica, 2.5 grams

Glycerol, 10.0 grams

Sorbitol Syrup, 23.0 grams (The syrup contains 70% sorbitol and 30% water by weight).

All components of the slurry are weighed into a beaker and dispersed for 2 minutes at 1500 rpm using a simple stirrer. A 110 mm×55 mm×3 mm sheet of standard clear cast acrylic Perspex®, grade 000, is used for the test, manufactured by Lucite International UK Ltd.

The test is carried out using a modified Wet Paint Scrub Tester produced by Sheen Instruments. The modification is to change the holder so that a toothbrush can be used in place of a paintbrush. In addition, a weight of 400 g is attached to the brush assembly, which weighs 145 g, to force the brush onto the PERSPEX® sheet. The toothbrush has a multi-tufted, flat trim nylon head with round ended filaments and medium texture, for example, the well-know Professional Mentadent® P gum health design, or an equivalent toothbrush.

A galvanometer is calibrated using a 45 Plaspec gloss head detector and a standard (50% gloss) reflecting plate. The galvanometer reading is adjusted to a value of 50 under these conditions. The reading of the fresh PERSPEX® sheet is then carried out using the same reflectance arrangement.

The fresh piece of PERSPEX® sheet is then fitted into a holder. 2 ml of the dispersed silica, sufficient to lubricate fully the brushing stroke, is placed on the sheet and the brush head is lowered onto the sheet. The machine is switched on and the sheet is subjected to 300 strokes of the weighted brush head. The sheet is removed from the holder and all the suspension is washed off. It is then dried and its gloss value is determined again. The abrasion value is the difference between the unabraded gloss value and the gloss value after abrasion.

This test procedure, when applied to known abrasives of the following weight median particle size, gave the following values:

Calcium Carbonate (15 μm) - 32
Silica xerogel (10 μm) prepared by method of UK 1264292 - 25
Alumina trihydrate (Gibbsite) (15 μm) - 16
Calcium Pyrophosphate (10 μm) - 14
Dicalcium diphosphate dihydrate (15 μm) - 7

Suitable precipitated silica particles of the invention will have a silica powder Radioactive Dentine Abrasion (RDA) value of less than 250, preferably less than 200, more preferably less than 150, even more preferably less than 130.

The Radioactive Dentine Abrasion Test (RDA) is also used as a monitor of the abrasiveness of abrasive systems for use in toothpastes. The method allows the measurement of the silica abrasive powder or an oral composition containing the silica abrasive powder. The procedure follows the method for assessment of oral composition abrasivity recommended by the American Dental Association (Journal of Dental Research 55 (4) 563, 1976). In this procedure extracted human teeth are irradiated with a neutron flux and subjected to a standard brushing regime. The radioactive phosphorous 32 removed from the dentine in the roots is used as the index of the abrasion of the powder or oral composition tested. A reference slurry containing 10 g of calcium pyrophosphate in 50 cm$^3$ of 0.5% aqueous solution of sodium carboxymethyl cellulose is also measured and the RDA of this mixture is arbitrarily taken as 100. The precipitated silica to be tested is prepared as a suspension at the same concentration as the pyrophosphate and submitted to the same brushing regime. This gives the RDA value for the silica abrasive powder.

In order to measure an RDA value for a dentifrice composition containing a silica of the invention or Comparative Example, a test slurry is prepared from 25 g dentifrice composition and 40 cm$^3$ of water and this slurry is submitted to the same brushing regime.

Suitable precipitated silica particles of the invention will have an Einlehener Abrasion Value of less than 10 mg/100,000 revolutions, preferably less than 8 mg/100,000 revolutions, more preferably less than 7 mg/100,000 revolutions, more preferably less then 6.5 mg/100,000 revolutions and most preferably less than 6 mg/100,000 revolutions.

The Einlehner method is another test used to measure the abrasiveness of particles. The Einlehner (E) Abrasion value is measured through the use of an Einlehner AT-1000 Abrader (Machine type 9452) provided by Hans Einlehner, Prufmaschinenbau, Industriestrasse 3a, D-86438 Kissing, Germany. In this test, a phosphorbronze screen is weighed and exposed to the action of a 10% aqueous silica suspension for a fixed number of revolutions, and the amount of abrasion is then determined as milligrams brass lost from the phosphorbronze screen per 100,000 revolutions. The phosphorbronze screen is of the long crimp kind having a fineness of 28 warp wires per cm and 24 weft wires per cm. The warp wire of phosphorbronze (composition: 91.5% Cu, 8.5% Sn) has a diameter of 0.21 mm, whereas the weft wire of tombak (bright annealed composition: 80% Cu, 20% Zn) has a diameter of 0.23 mm. The fabric thickness is 0.49 mm. The standard test screen has a circular shape of 50 mm diameter. The edges must be broken.

Specifically, phosphorbronze screens are prepared by washing in hot, soapy water in an ultrasonic bath for 5 minutes, then rinsed in tap water and rinsed again in a beaker containing 150 ml water set in an ultrasonic bath. The screen is rinsed again in tap water, dried in an oven set at 105° C. for 20 minutes, cooled in a desiccator and weighed by means of an analytical balance to an accuracy of 0.1 mg. The standard test screen must not be touched with bare fingers prior to weighing. The Einlehner test cylinder is assembled with a wear plate and weighed screen and clamped in place, with the abrasion side facing upwards (line marked on screen downwards). The wear plate is used for about 25 tests or until worn badly; the weighed screen is used only once.

A 10% silica slurry, prepared by mixing 100 g silica with 900 g deionized water, is poured into the Einlehner test cylinder. Einlehner PVC tubing is placed onto the agitating shaft. The PVC tubing has 5 numbered positions. For each test, the position of the PVC tubing is incremented until it has been used five times, then discarded. The Einlehner abrasion instrument is re-assembled and the instrument set to run for 174,000 revolutions.

After the cycle is completed, the screen is removed rinsed in tap water, placed in a beaker containing water and set in an ultrasonic bath for 2 minutes, rinsed with deionized water and dried in an oven set at 105° C. for 20 minutes. The dried screen is cooled in a desiccator and reweighed with the same accuracy and handling precautions. Two tests are run for each sample and the results are averaged and expressed in mg lost per 100,000 revolutions. The result, measured in units of mg lost per 100,000 revolutions, for a 10% slurry can be characterized as the 10% Einlehner (E) abrasion value.

Suitable precipitated silica particles of the invention will have a surface area measured by BET of at least 10 m$^2$/g, preferably at least 50 m$^2$/g. Suitably, the surface area measured by BET is at most 900 m²/g, preferably at most 600 m²/g, more preferably at most 550 m²/g. A particularly preferred range of surface area is from 10 to 550 m²/g Surface area is determined using standard nitrogen adsorption methods of Brunauer, Emmett and Teller (BET) J. Amer. Chem. Soc. 60, 309 (1938), using a single point method with a Sorpty 1750 apparatus supplied by Carlo Erba company of Italy. The sample is outgassed under vacuum at 270° C. for 1 hour before measurement.

The precipitated silica particles of the invention have an oil absorption value of less than 150 cm³/100 g, preferably less than 130 cm³/100 g, even more preferably less than 110 cm³/100 g, most preferably less than 100 cm³/100 g. Even lower values are preferred such as less than 85 cm³/100 g more preferably less than 75 cm³/100 g, even more preferably less than 70 cm³/100 g.

The precipitated silica particles of the invention have an oil absorption value of at least 20 cm³/100 g, preferably of at least 30 cm³/100 g, and even more preferably of at least 40 cm³/100 g.

The oil absorption (O/A) is determined by the ASTM spatula rub-out method (American Society of Test Material Standards D 281).

The test is based upon the principle of mixing linseed oil with a silica by rubbing with a spatula on a smooth surface until a stiff putty-like paste is formed which will not break or separate when it is cut with the spatula. The volume of oil used is then put into the following equation:

$$\text{Oil absorption value} = (\text{cm}^3 \text{ oil absorption} \times 100)/(\text{weight of silica in grams})$$

The oil absorption value is expressed as cm³/100 g.

A second aspect of the invention provides an oral composition, preferably a toothpaste, comprising amorphous precipitated silica particles of the invention as described hereinbefore.

When an oral composition is prepared using the silica particles of this invention, the particles will usually be in the form of a substantially dry free flowing particulate material before incorporation into the oral composition.

The oral composition may contain one or more additional components, as will now be described.

Oral compositions of the invention preferably comprise one or more surfactants, preferably selected from anionic, nonionic, amphoteric and zwitterionic surfactants, and mixtures thereof, all being suitable for dental and/or oral use.

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Example of preferred anionic surfactants may include sodium lauryl sulphate, sodium dodecylbenzene sulphonate, sodium lauroyl sarcosinate and sodium coconut monoglyceride sulphonate.

Nonionic surfactants which may be suitable for use in composition of the invention include sorbitan and polyglycerol esters of fatty acids, as well as ethylene oxide/propylene oxide block copolymers.

Amphoteric surfactants which may be suitable for use in compositions of the invention include betaines such as cocamidopropyl betaine, and sulphobetaines, for example.

The surfactant or surfactant mixture is suitably present in the oral composition in a total amount of from 0.1 to 3% by weight.

Water is another preferred component of the oral compositions of the invention and may be present in an amount of from 1 to 90% by weight, preferably from 10 to 50%.

Toothpastes and creams of this invention may also contain humectants, for example polyols such as glycerol, sorbitol syrup, polyethylene glycol, lactitol, xylitol and hydrogenated corn syrup. The total amount of humectant, if present, may be for example in the range of from 10 to 85% by weight of the composition.

In the oral compositions of the present invention it is particularly preferred that one or more thickening agents and/or suspending agents are included, in order to give the composition the desired physical properties (e.g. whether a paste, cream or a liquid)

A particularly preferred means for thickening the oral compositions of the invention is by the inclusion of conventional thickening materials such as thickening silicas, for example, the high structure silica Sorbosil TC15™ with an oil absorption above 250 cm³/100 g from Ineos Silicas Ltd.

Other suitable suspending/thickening agents are well known in the art and include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), heteropolysaccharide gums, guar gums and cellulose derivatives such as sodium carboxymethyl cellulose.

The thickening agent and/or suspending agent (which may be used singly or as mixtures of two or more such materials) may be present in the composition in a total amount of from 0.1 to 50% by weight; preferably from 5 to 15% for silica thickening agents; preferably from 0.1 to 5% for polymer suspending agents.

An oral composition containing the precipitated amorphous silica particles according to the present invention may also include a fluoride ion source as protection against demineralisation by bacteria (caries) and/or acidic components of the diet (erosion).

The fluoride ion source may be provided by any of the compounds conventionally used in toothpastes for these purposes, e.g. sodium fluoride, alkali metal monofluorophosphate, stannous fluoride aminefluorides and the like, with an alkali metal monofluorophosphate such as sodium monofluorophosphate being preferred. The fluoride ion source serves in a known manner for caries protection. Preferably, the fluoride ion source will be used in an amount to provide a safe yet effective amount to provide an anti-caries and anti-erosion benefit, such as an amount sufficient to provide from 25 ppm to 3500 ppm, preferably 1100 ppm, as fluoride ion. For example the formulation may contain from 0.1 to 0.5 wt % of an alkali metal fluoride such as sodium fluoride.

The oral composition may contain one or more other components conventionally found in oral compositions. Suitable additional ingredients include: flavouring substances, e.g. peppermint, spearmint; artificial sweeteners; perfume or breath freshening substances; pearlescing agents; tooth whitening agents and peroxy bleaching agents e.g. hydrogen peroxide or peracetic acid; stabilising agents for peroxy bleaches e.g. dipicolnic acid or sodium stannate; opacifiers; pigments and colourings; preservatives; moisturising agents; anti-caries agents; anti-plaque agents; plaque buffers such as urea, calcium lactate, calcium glycerophosphate, strontium polyacrylates; anti-calculus agents such as alkali metal pyrophosphates, hypophosphite-containing polymers, organic phosphonates, phosphocitrates etc.; anti-bacterial agents such as Triclosan (ex Ciba Geigy), chlorhexidine and cetyl pyridinium chloride, polymeric compounds which can enhance the delivery of active ingredients such as anti-bacterial agents e.g.copolymers of polyvinylmethylether with maleic anhydride and other similar delivery enhancing polymers, e. g. those described in DE-A-3, 942, 643 (Colgate); therapeutic agents such as copper-, zinc- and stannous salts e.g. zinc citrate, sodium zinc citrate and stannous pyrophosphate, sanguinarine extract, metronidazole; tooth desensitizing agents such as potassium or strontium salts, e.g. potassium nitrate or strontium chloride; anti-inflammatory agents such as ibuprofen, flurbiprofen, aspirin, indomethacin etc; proteins; vitamins such as Vitamin C; functional biomolecules such as bacteriocins, antibodies, enzymes; plant extracts; salts; pH adjusting agents.

Other optional ingredients that may be included are e.g. bleaching agents, e.g. those described in EP-A-0, 545, 594, effervescing systems such as sodium bicarbonate/citric acid systems, colour change systems, and so on.

Preferably the pH of the oral composition incorporating the silica particles of the present invention is from 6 to 10.5.

The silica particles of the present invention may be incorporated in an orally acceptable carrier to produce an oral composition. The term "orally acceptable carrier" means a suitable vehicle which can be used to apply the resulting oral composition to the oral cavity in a safe and effective manner. The silica particles are incorporated at an effective level such that they provide cleaning.

The oral composition, such as a toothpaste of the present invention, may be formulated into a single formulation, or it may be formulated for multi compartment containers into different formulations to produce for instance a striped formulation.

Oral compositions, such as toothpastes of the invention suitably comprise from 0.5 to 50% by weight of the silica particles of the invention as detailed hereinbefore, preferably 1 to 25%, more preferably from 1 to 15%, most preferably 1 to 10%.

The silica particles of the invention may be the sole or substantially the sole abrasive cleaning aid in the oral composition or toothpaste, meaning that no other abrasive particles are included at levels which would substantially modify the cleaning or abrasion performance of the oral composition or toothpaste (i.e. causing a 10% or more change in cleaning or abrasion as measured herein compared to a composition containing the particles of the invention alone), or the silica particles of the invention may be used in combination with other abrasives in order to improve the cleaning of the composition without excessive additional abrasion over that caused by the other abrasive. Surprisingly, the particles of the invention can give excellent cleaning without excessive abrasion, at comparatively low inclusion levels and without the need for other abrasive cleaning particles in an oral composition such as a toothpaste. When silica particles of the invention are used as a cleaning booster in conjunction with other dental abrasive particles, the silica particles of the invention are present as from 1%, preferably from 4%, more preferably from 5%, even more preferably from 8%, most preferably from 10% by weight of the abrasive particles of the oral composition. Suitably, the silica particles of the invention are present as up to 90%, preferably up to 60%, more preferably up to 60%, even more preferably up to 50%, most preferably up to 40% by weight of the abrasive particles of the oral composition. A particularly preferred range is from 8 to 40% by weight of the abrasive.

The cleaning behaviour of toothpastes of the invention, comprising particles of the invention, and of comparative examples, is assessed by means of the FT cleaning test described below.

FT Cleaning Test

The test is fully described in "Dental stain prevention by abrasive toothpastes: A new in vitro test and its correlation with clinical observations", P. L. Dawson et al., J. Cosmet. Sci., 49, 275-283 (1998). The test can be carried out on the full toothpaste system as described in the reference, but it can also be carried out on an abrasive slurry in order to compare the cleaning performance of different abrasive types. In this latter case, precipitated amorphous silica particles of the invention can be compared for cleaning performance against reference silicas.

As confirmation of performance benefit, toothpastes containing silicas of the invention have also been formulated to demonstrate cleaning superiority over toothpastes containing reference silicas, Substrate A substrate consisting of highly polished 17 mm sintered, pure hydroxyapatite (HAP) discs is prepared. The discs are polished using a Buehler rotary grinder and P600 wet paper, followed by P1200 lapping paper to give a mirror-like finish to simulate enamel tooth surface. The whiteness of the discs (using the CIE 1976 L*a*b* system) before cleaning, L* (clean), is then measured using a Minolta Chroma-meter CR200, which has been calibrated against a standard calibration tile.

Staining

A fresh staining solution is prepared by mixing 50 g of a 0.5% by weight solution of tannic acid and 50 g of a 0.5% by weight solution of ammonium ferric sulphate to form a fresh colloidal iron (iii) tannic acid complex ("ferric tannate"), which has a dark colour. The fresh mixture is painted onto the HAP discs using a fine squirrel-hair brush and gently dried with a warm hairdryer. A sufficient number of coats of staining solution are applied in order to produce a darkness measurement of L*=50 +/−5 as determined using a Minolta Chroma-meter CR200. This value is designated L* (soiled)

Toothpaste Slurry Preparation:

A diluent is prepared, which consists of:

| | % by weight |
|---|---|
| Sodium carboxymethyl cellulose (SCMC 7M) | 0.5 |
| Glycerol | 5.0 |
| Formalin | 0.1 |
| Demineralised Water | 94.4 |

Water and glycerol are first added, then the formalin and SCMC with gentle agitation using a Heidolph stirrer. It should be ensured that the SCMC has fully hydrated. The toothpaste under test is weighed into a plastic beaker (diameter 4.5 cm×height 10 cm) and mixed with diluent and demineralised water in the following proportions by weight to give a 100 g toothpaste slurry sample:

Toothpaste 33.3%; Diluent 33.3%; Water 33.3% to produce a 100 g toothpaste slurry preparation, which is mixed for one minute with a high shear Heidolph mixer at 4000 r.p.m. It is ensured that the toothpaste is evenly distributed throughout the diluent. The toothpaste slurry is prepared immediately prior to carrying out the test to avoid the abrasive particles settling out from the slurry.

Silica Slurry Preparation

A diluent is prepared, which consists of:

|  | % by weight |
|---|---|
| Xanthan Gum Kelzan M (Kelco) | 0.35 |
| Sodium Lauryl Sulphate (Empicol 045, Albright & Wilson) | 0.50 |
| Demineralised Water | 99.15 |

The Keizan is gently mixed in the water, using a Heidolph stirrer, to ensure full hydration. The sodium lauryl sulphate (SLS) is then added at low stirrer speed to prevent foaming.

The amount of silica used in the test is determined by the expected loading in a toothpaste and is usually measured at 1% or 3.3% or 6%. This will correspond to toothpaste loadings of 3%, 9.9% and 18% respectively i.e. 3 times the silica test loading. More efficient silicas should be assessed at lower loadings in order to more readily differentiate performance benefits.

The silica under test is weighed into a plastic beaker (diameter 4.5 cm×height 10 cm). The weight will depend upon the silica loading chosen and will be based upon preparing 100 g of total silica slurry preparation. Diluent is added up to 100 g. Mix together for one minute using a Heidolph mixer at high shear (4000 r.p.m.). It is ensured that the silica is evenly distributed throughout the diluent. The slurry should only be prepared immediately prior to carrying out the test to avoid the abrasive particles settling out from the slurry.

Brushing:

The stained HAP discs are then mounted horizontally in the bottom of a trough containing the toothpaste slurry or silica slurry under test and 263 g weighted Mentadent ® P Professional soft-nylon flat trim toothbrush heads are oscillated over the disc surfaces using a mechanical scrubbing machine (modified Martindale abrasion tester). An oscillation rate of 150 cycles per minute is used. The toothbrush heads are 34-tuft flat-trim 0.2 mm bristle nylon heads and are weighted via weights loaded onto vertical spindles mounted in linear ball bearings. Soil removal after 50, 100 and 150 oscillations was monitored, corresponding to an $FT_{50}$, FT100 and $FT_{150}$. Removal test result respectively. The whiteness of the HAP discs after cleaning, L* (cleaned) is measured using a Minolta Chroma-meter CR200. As detailed in the test reference above, a convenient simple expression of comparative abrasive performance is taken to be the percentage clean or removed at 100 oscillations ($FT_{100}$ defined as the % $FT_{100}$ Removal where:

$$\% FT_{100} \text{ Removal} = \frac{(L^*(\text{cleaned}) - L^*(\text{soiled}))}{(L^*(\text{clean}) - L^*(\text{soiled}))} \times 100$$

Toothpaste Cohesion

The cohesion of a toothpaste is a good measure of the "stand-up" properties of the ribbon when it has been extruded from a toothpaste tube onto a toothbrush. Higher cohesion values indicate firmer toothpaste ribbons, whereas low cohesion numbers are obtained from low viscosity, poorly structured toothpastes, which quickly sag into the bristles of the brush. It is generally required that a toothpaste has a cohesion within the range of 150-430 g to provide a good quality, extrudable ribbon, which does not sag and is not too firm.

The basic principle of the test is to measure the weight in grams required to pull two parallel plates apart, which have a specific layer of toothpaste sandwiched between them. The purpose built equipment consists of:

1) A spring balance in which the spring can be extended from 0-430 g in 100 mm of length. The spring has a calibration scale of zero to 430 g in 10 g intervals and can be adjusted to zero at the start of the test.
2) A motor driven ratchet, which is attached to the bottom plate and can be used to apply a constant, uniform, smooth vertical pull on the bottom plate of 5 cm per minute.
3) An upper polished chrome circular plate of 64 mm diameter, which has a hook on the upperside that can be attached to the spring balance. The polished plate has three small identical spacer pieces of polished chrome on the underside of the plate, as an integral part of the plate. These protrude to a depth of 4 mm, which determines the toothpaste film thickness when the equipment is assembled to carry out the test.
4) A lower polished chrome circular plate of 76 mm diameter, which is attached underneath to a motor driven ratchet. Two short pegs are located on the top of the plate so that the top plate can be positioned on the bottom plate concentrically from the centres.
5) A metal framework which allows the top plate to be situated concentrically above the bottom plate and the bottom plate to be adjusted so that the plate is approximately horizontal (achieved through the use of levelling feet on the base of the equipment).

15-20 g of toothpaste is evenly distributed onto the underside of the upper plate and the plate is carefully positioned onto the top of the bottom plate, using the two short pegs to locate the edge of the top plate. The top plate is firmly pressed down onto the bottom plate, until all three spacers have made contact with the bottom plate. Excess toothpaste, which has been squeezed out from between the two plates is then removed with a spatula, such that no toothpaste extends beyond the diameter of the top plate. The upper plate is then connected to the spring balance and the scale set to zero grams. The equipment is then switched on to allow the motor driven ratchet to lower the bottom plate. The spring is gradually extended and the highest observed weight is noted, as the two parallel plates sandwiched with toothpaste are eventually pulled apart. This is the toothpaste cohesion recorded in grams.

A further aspect of the invention is the use of the amorphous silica particles of the invention as an abrasive cleaning aid in an oral composition, particularly in a toothpaste.

Another aspect of the invention is a process for reducing the abrasivity of amorphous precipitated silica for use in an oral composition comprising comminuting and classifying the amorphous precipitated silica to form amorphous precipitated silica particles with a weight median particle diameter $d_{50}$ of less than 3 µm and a $d_{90}$ value, wherein 90% by weight of the particles have a diameter less than the $d_{90}$ value, of 6 µm or less. The preferred features of the precipitated amorphous silica particles of the first aspect of the invention also apply to this aspect of the invention.

The invention will be now further illustrated but not limited by the following examples.

EXAMPLE 1

A silica was prepared according to the details of Example 3 of EP 0 318 165, except for some minor changes outlined below:

A heated stirred reaction vessel was used for the silicate/acid reaction. The solutions used in the process were as follows:

i) Sodium silicate solutions having a $SiO_2:Na_2O$ ratio by weight of 3.3:1 and an $SiO_2$ concentration of 16.6% w/w.
ii) A sulphuric acid solution of specific gravity 1.12 (17.1% w/w solution in water)
iii) An electrolyte solution of 25% w/w NaCl in water.

109 liters of water were placed in a 325 liters vessel together with 34.7 liters of electrolyte solution and 1.0 liter sodium silicate solution. This mixture was then stirred and heated to 50° C. A further 100.3 liters of sodium silicate solution and sulphuric acid (39 liters) were then added simultaneously over a period of about 20 minutes with stirring while maintaining the temperature at 50° C. The flow rates of the silicate and acid solutions were uniform throughout the addition period to ensure that a constant pH was maintained in the vessel. Further sulphuric acid solution was then added over a period of 10 minutes with continued mixing to reduce the pH of the liquid to the range of 3.0 to 3.5. During this addition of acid the temperature was maintained. The resultant slurry was then filtered and washed with water to remove excess electrolyte, such that the residual electrolyte was less than 2% on a dry weight basis.

After washing, the filter cake was flash dried to a physical moisture content of 4.5% and comminuted to a range of different particle sizes as follows:

Comparative Example 1A was not milled at all and had a weight median particle diameter, $d_{50}$ of 15.6 μm and a $d_{90}$ value of 32.5 μm.

Comparative Example 1B was milled using a Circoplex hammer mill with built in classifier and had a weight median particle diameter, $d_{50}$ of 7.8 μm and a $d_{90}$ value of 17.3 μm.

Comparative Example 1C was micronised using a fluidised bed air jet mill with internal classifier and had a weight median particle diameter, $d_{50}$ of 3.5 μm and a $d_{90}$ value of 6.7 μm.

Example of the Invention 1D was micronised by a pancake air microniser with internal classifier and had a weight median particle diameter, $d_{50}$ of 2.4 μm and a $d_{90}$ value of 4.3 μm. Example of the Invention 1E was micronised by a pancake air microniser with internal classifier and had a weight median particle diameter, $d_{50}$ of 2.0 μm and a $d_{90}$ value of 3.6 μm.

EXAMPLE 2

A sample of Sorbosil AC35™ (Comparative Example 2A) produced by Ineos Silicas Ltd using a hammer mill with built in classifier has a weight median particle diameter, $d_{50}$ of 10.4 μm and a $d_{90}$ value of 37.9 μm.

This material was micronised using a pancake air microniser to a weight median particle diameter, $d_{50}$ of 2.1 μm, a $d_{90}$ value of 4.9 μm and designated Example 2B of this Invention.

EXAMPLE 3

A sample of Sorbosil AC77™ (Comparative Example 3A) produced by Ineos Silicas Ltd using a hammer mill with built in classifier has a weight median particle diameter, $d_{50}$ of 8.1 μm and a $d_{90}$ value of 20.2 μm.

This material was micronised using a pancake air microniser to a weight median particle diameter, $d_{50}$ of 2.9 μm, a $d_{90}$ value of 6.2 μm and designated Comparative Example 3B.

This material was also micronised using a pancake air microniser to a weight median particle diameter, $d_{50}$ of 1.9 μm, a $d_{90}$ value of 4.2 μm and designated Example 3C of the Invention.

EXAMPLE 4

A silica was prepared according to the details of Example 2 of US Pat. No. 5,447,704A. After drying to a moisture content of 5%, the silica was micronised to a range of different particle sizes, as follows:

Comparative Example 4A was micronised using a fluidised bed air jet mill with internal classifier and had a weight median particle diameter, $d_{50}$ of 4.6 μm and a $d_{90}$ value of 9.9 μm.

Comparative Example 4B was micronised by a pancake air microniser with internal classifier and had a weight median particle diameter, $d_{50}$ of 3.3 μm and a $d_{90}$ value of 6.6 μm.

Comparative Example 4C was micronised by a pancake air microniser with internal classifier and had a weight median particle diameter, $d_{50}$ of 2.6 μm and a $d_{90}$ value of 5.0 μm.

Comparative Example 4D was micronised by a pancake air microniser with internal classifier and had a weight median particle diameter, $d_{50}$ of 1.9 μm and a $d_{90}$ value of 4.1 μm.

Table 1 details important physical properties of the silicas produced from Examples 1 to 4 and compares them to silicas with the same general structure, but with particle size distributions not corresponding to those of the silica particles of this invention.

Table 2 shows the FT Cleaning test data for Examples 1 and 4 silicas at 1% silica loading in the silica slurry test.

Table 3 shows the FT Cleaning test data for Example 2 and 3 silicas at 3.3% silica loading in the silica slurry test.

TABLE 1

| Sample | $d_{10}$ μm | $d_{50}$ μm | $d_{90}$ μm | $d_{99}$ μm | O/A cm³/100 g | PAV | Silica RDA | Einlehner Abrasion Value mg/100,000 revs |
|---|---|---|---|---|---|---|---|---|
| Comparative Ex 1A | 1.8 | 15.6 | 32.5 | 48.8 | 68 | 21.9 | | 5.4 |
| Comparative Ex 1B | 1.5 | 7.8 | 17.3 | 26.2 | 65 | 19.5 | | 4.8 |
| Comparative Ex 1C | 1.2 | 3.5 | 6.7 | 9.4 | 65 | 13.4 | 150 | 4.6 |
| Ex 1D of Invention | 0.7 | 2.4 | 4.3 | 9.9 | 69 | 6.2 | 119 | 2.5 |
| Ex. 1E of Invention | 0.6 | 2.0 | 3.6 | 5.0 | 66 | 7.6 | 112 | 2.2 |
| Comparative Ex 2A | 1.7 | 10.4 | 37.9 | 68.4 | 82 | 9.8 | | 6.0 |
| Ex 2B of Invention | 0.5 | 2.1 | 4.9 | 8.0 | 67 | 8.1 | | 4.0 |
| Comparative Ex 3A | 2.4 | 8.1 | 20.2 | 38.1 | 108 | 17.8 | | 7.0 |
| Comparative Ex 3B | 0.6 | 2.9 | 6.2 | 10.8 | 96 | 13.6 | | 6.1 |
| Ex 3C of Invention | 0.4 | 1.9 | 4.2 | 6.5 | 92 | 9.6 | | 4.5 |
| Comparative Ex 4A | 1.3 | 4.6 | 9.9 | 14.5 | 58 | 28.7 | 329 | 12.8 |
| Comparative Ex 4B | 0.7 | 3.3 | 6.6 | 9.3 | 50 | 20 | 280 | 11.6 |
| Comparative Ex 4C | 0.5 | 2.6 | 5.0 | 6.9 | 50 | 15.3 | 245 | 6.4 |
| Comparative Ex 4D | 0.4 | 1.9 | 4.1 | 6.9 | 68 | 9.4 | 182 | 6.2 |

TABLE 2

| Sample | $d_{50}$ μm | $d_{90}$ μm | $d_{99}$ μm | $FT_{50}$ @ 1% Silica Loading | $FT_{100}$ @ 1% Silica Loading | $FT_{150}$ @ 1% Silica Loading |
|---|---|---|---|---|---|---|
| Comparative Ex 1A | 15.6 | 32.5 | 48.8 | 72.5 | 81.1 | 85 |
| Comparative Ex 1B | 7.8 | 17.3 | 26.2 | 77 | 85.3 | 87.8 |
| Comparative Ex 1C | 3.5 | 6.7 | 9.4 | 78.8 | 83.2 | 85.8 |
| Ex 1D. of Invention | 2.4 | 4.3 | 9.9 | 79.7 | 84.9 | 86.8 |
| Ex. 1E of Invention | 2.0 | 3.6 | 5.0 | 83 | 87.6 | 89.5 |
| Comparative Ex 4A | 4.6 | 9.9 | 14.5 | 81.8 | 88 | 90.1 |
| Comparative Ex 4B | 3.3 | 6.6 | 9.3 | 81.2 | 86.9 | 89.2 |
| Comparative Ex. 4C | 2.6 | 5.0 | 6.9 | 81.4 | 88.0 | 89.4 |
| Comparative Ex. 4D | 1.9 | 4.1 | 6.9 | 81 | 85.3 | 87.6 |

TABLE 3

| Sample | $d_{50}$ μm | $d_{90}$ μm | $d_{99}$ μm | $FT_{50}$ @ 3.3% Silica Loading | $FT_{100}$ @ 3.3% Silica Loading | $FT_{150}$ @ 3.3% Silica Loading |
|---|---|---|---|---|---|---|
| Comparative Ex 2A | 10.4 | 37.9 | 68.4 | 53 | 74.3 | 78.8 |
| Ex 2B. of Invention | 2.1 | 4.9 | 8.0 | 57.1 | 79.8 | 83 |
| Comparative Ex 3A | 8.1 | 20.2 | 38.1 | 55.6 | 77.9 | 84.3 |
| Ex 3C. of Invention | 1.9 | 4.2 | 6.5 | 66.6 | 83 | 86.6 |

It can be seen from the results in the tables that reducing the $d_{50}$ particle diameter to less than 3 μm and the $d_{90}$ particle diameter to 6 μm or less for each of the precipitated silicas yields a reduction in abrasivity, compared to the larger particle size silica, as monitored by PAV, RDA and Einlehner, whilst the cleaning efficacy surprisingly either remains the same or shows an improvement as monitored by the $FT_{100}$ values.

EXAMPLE 5

Two silicas of Example 1 (Comparative Example 1C and Example 1E of the invention) were separately introduced into the oral composition formulation Table 4.

TABLE 4

| Ingredient | % w/w |
|---|---|
| Sorbitol | 45 |
| Toothpaste thickener Sorbosil TC15 ™ | 8.0 |
| Standard toothpaste abrasive Sorbosil AC35 ™ | 10.0 |
| Comparative Example 1C or Example of the invention 1E | 3.0 |
| Water | 24.28 |
| PEG 1500 | 5.0 |
| Sodium Lauryl Sulphate | 1.5 |
| Titanium dioxide | 1.0 |
| SCMC | 0.7 |
| Flavour | 1.0 |
| NaF | 0.22 |
| Sodium saccharin | 0.2 |
| Sodium benzoate | 0.1 |

Sorbosil AC35™ (also Comparative Example 2A) produced by Ineos Silicas Ltd has a weight median particle diameter of 10.4 μm.
Sorbosil TC15™ is a highly structured precipitated silica with an oil absorption value greater than 250 cm³/100 g.
PEG 1500 is polyethylene glycol with a mean molecular weight of 1500.
SCMC is sodium carboxymethyl cellulose
Comparative example 5A is the toothpaste containing Comparative Example 1C
Example 5B is the toothpaste containing Silica 1E of the invention The two toothpastes were measured for RDA as detailed hereinbefore and evaluated in the FT Cleaning test. The results are given in Table 5.

TABLE 5

| Toothpaste Identitity | $FT_{50}$ | $FT_{100}$ | $FT_{150}$ | Toothpaste RDA | Toothpaste Cohesion |
|---|---|---|---|---|---|
| Comparative Example 5A | 52.4 | 69.8 | 73.7 | 114 | 140 |
| Example 5B | 54.2 | 79.0 | 82.6 | 92 | 150 |

It can be seen from table 5 that example 5B, containing the silica according to the invention, provides better cleaning and lower abrasion, as measured by RDA, than comparative example 5A, which contains the same silica, but with a particle size distribution falling outside that of the invention.

EXAMPLE 6

Two silicas from Example 1 (Comparative Example 1C and Example 1D of the invention) were separately introduced into the transparent oral composition formulation in Table 6.

TABLE 6

| Ingredient | % w/w |
|---|---|
| Sorbitol | 73.0 |
| Toothpaste thickener Sorbosil TC15 ™ | 10.0 |
| Comparative Example 1D or Example of the invention 1E | 4.0 |
| Water | 6.58 |
| PEG 1500 | 3.0 |
| Sodium Lauryl Sulphate | 1.5 |
| SCMC | 0.5 |
| Flavour | 1.0 |
| NaF | 0.22 |
| Sodium Saccharin | 0.2 |

Comparative example 6A is the toothpaste containing Comparative Example 1C Example 6B is the toothpaste containing Silica 1D of the invention
The two toothpastes were measured for RDA as detailed hereinbefore and evaluated in the FT Cleaning test. The results are given in Table 7

TABLE 7

| Toothpaste Identity | $FT_{50}$ | $FT_{100}$ | $FT_{150}$ | Toothpaste RDA | Toothpaste Cohesion |
|---|---|---|---|---|---|
| Comparative Example 6A | 36.5 | 59.2 | 67.4 | 78 | 145 |
| Example 6B | 54.3 | 77.6 | 81.2 | 58 | 150 |

It can be seen from table 7 that example 6B, containing the silica according to the invention, provides better cleaning and lower abrasion, as measured by RDA, than comparative example 6A, which contains the same silica, but with a particle size distribution falling outside that of the invention.
It can be seen from the results in the tables that reducing the $d_{50}$ particle diameter to less than 3 μm and the $d_{90}$ particle diameter to 6 μm or less for the precipitated silicas of example 1 yields an improved toothpaste cleaning efficacy, as monitored by the $FT_{100}$ values, yet reduced abrasivity as monitored by PAV, RDA and Einlehner.

The invention claimed is:

1. Amorphous precipitated silica particles with an oil absorption value of 85 cm³/100 g or less, a weight median particle diameter $d_{50}$ of less than 3 μm and a $d_{90}$ value, wherein 90% by weight of the particles have a diameter less than the $d_{90}$ value, of 5 μm or less, a $d_{99}$ value, wherein 99% by weight of the particles have a diameter less than the $d_{99}$ value, of 10 μm or less and wherein the Radioactive Dentine Abrasion value for the particles is less than 150, wherein an abrasive slurry of the silica particles has a $FT_{100}$ cleaning result that is greater than or equal to 75% and the perspex abrasion value for the particles is less than 10.

2. The amorphous precipitated silica particles according to claim 1 wherein the weight media particle diameter $d_{50}$ is less than 2.5 μm.

3. The amorphous precipitated silica particles according to claim 1 wherein the $d_{50}$ value is 0.5 μm or more and the $d_{90}$ value is 2 μm or more.

4. The amorphous precipitated silica particles according to claim 1 wherein the Einlehner Abrasion Value for the particles is less than 10 mg/100,000 revolutions.

5. The amorphous precipitated silica particles according to claim 4 wherein the Einlehner Abrasion Value for the particles is less than 7 mg/100,000 revolutions.

6. The amorphous precipitated silica particles according to claim 1 wherein the BET surface area of the particles is from 10 to 900 m²/g.

7. The amorphous precipitated silica particles according to claim 1 wherein the oil absorption value of the particles is from 20 to 100 cm³/100 g.

8. An oral composition comprising an orally acceptable carrier and an effective cleaning amount of amorphous precipitated silica particles according to claim 1.

9. The oral composition according to claim 8 comprising from 0.5 to 50% by weight of the amorphous precipitated silica particles.

10. The oral composition according to claim 8 wherein the amorphous precipitated silica particles are present as substantially the sole abrasive in the oral composition.

11. The oral composition according to claim 8 comprising abrasive particles wherein the amorphous precipitated silica particles are present as 1 to 90% by weight of the abrasive particles of the oral composition.

12. The oral composition according to claim 8 which is a toothpaste.

13. The oral composition according to claim 12 wherein the toothpaste has a Radioactive Dentine Abrasion value of less than 150.

14. A method for providing an abrasive cleaning aid in an oral composition comprising using amorphous precipitated silica particles according as claimed in claim 1.

15. The method of claim 14 wherein the oral composition is a toothpaste.

16. A process for reducing the abrasivity of an amorphous precipitated silica for use in an oral composition comprising: comminution by jet, opposed jet, pancake or fluidised bed micronisation; and classifying the silica; whereby amorphous precipitated silica particles according to claim 1 are formed.

17. Amorphous precipitated silica particles with an oil absorption value of 150 cm³/100 g or less, a weight median particle diameter $d_{50}$ less than 3 μm and a $d_{90}$ value, wherein 90% by weight of the particles have a diameter less than the $d_{90}$ value, of 5 μm or less, wherein the Radioactive Dentine Abrasion value for the particles is less than 130, wherein an abrasive slurry of the silica particles has a $FT_{100}$ cleaning result that is greater than or equal to 75% and the perspex abrasion value for the particles is less than 10.

18. The amorphous precipitated silica particles according to claim 17 wherein the particles have a $d_{99}$ value, wherein 99% by weight of the particles have a diameter less than the $d_{99}$ value, of 12 μm or less.

19. The amorphous precipitated silica particles according to claim 17 wherein the weight median particle diameter $d_{50}$ is less than 2.5 μm.

20. The amorphous precipitated silica particles according to claim 17 wherein the $d_{99}$ value is 10 μm or less.

* * * * *